(12) United States Patent
Green

(10) Patent No.: US 10,602,850 B2
(45) Date of Patent: Mar. 31, 2020

(54) PORTABLE MEDICAL ARMREST

(71) Applicant: Christopher Corey Green, Pontiac, MI (US)

(72) Inventor: Christopher Corey Green, Pontiac, MI (US)

( * ) Notice: Subject to any disclaimer, the term of this patent is extended or adjusted under 35 U.S.C. 154(b) by 0 days.

(21) Appl. No.: 15/609,579

(22) Filed: May 31, 2017

(65) Prior Publication Data
US 2020/0022500 A1 Jan. 23, 2020

(51) Int. Cl.
*A47C 16/00* (2006.01)
*F16B 1/00* (2006.01)
*A61G 5/12* (2006.01)

(52) U.S. Cl.
CPC .............. *A47C 16/00* (2013.01); *A61G 5/125* (2016.11); *F16B 1/00* (2013.01); *F16B 2001/0028* (2013.01)

(58) Field of Classification Search
USPC .......................................................... 248/118
See application file for complete search history.

(56) References Cited

U.S. PATENT DOCUMENTS

| | | | | | |
|---|---|---|---|---|---|
| 3,234,623 | A | * | 2/1966 | Rector | A61G 17/04 248/118 |
| 4,265,232 | A | * | 5/1981 | Stonich | A61F 5/37 128/877 |
| 5,149,033 | A | * | 9/1992 | Burzler | A61G 7/0755 248/118 |
| 5,173,979 | A | * | 12/1992 | Nennhaus | A61G 7/0755 5/490 |
| 5,216,771 | A | * | 6/1993 | Hoff | A47C 20/021 5/490 |
| 5,335,888 | A | * | 8/1994 | Thomsen | A47B 21/0371 2/16 |
| 5,418,991 | A | * | 5/1995 | Shiflett | A47C 20/021 5/647 |
| 5,716,334 | A | * | 2/1998 | Wade | A61F 5/0585 128/882 |
| 5,829,079 | A | * | 11/1998 | Castro | A47G 9/10 5/636 |
| 5,918,839 | A | * | 7/1999 | DuBois | A47B 21/0371 248/118 |
| 6,179,756 | B1 | * | 1/2001 | Bertolucci | A63B 21/0023 482/131 |
| D438,624 | S | * | 3/2001 | Reina | D24/190 |
| 6,438,779 | B1 | * | 8/2002 | Brown | A47C 20/021 128/845 |

(Continued)

*Primary Examiner* — Monica E Millner
(74) *Attorney, Agent, or Firm* — Young Basile Hanlon & MacFarlane, P.C.

(57) ABSTRACT

A portable medical apparatus for supporting a patient's arm having a top surface, a bottom surface, a peripheral surface, and an outer layer. The top surface has a front edge and a back edge opposite the front edge. The top surface defines a concave depression that extends into the top surface and slopes downward from the back edge to the front edge. The bottom surface is opposite the top surface. The peripheral surface connects the top surface to the bottom surface. The outer layer is connected to a portion of the peripheral surface and defines a pocket between the outer layer and the portion of the peripheral surface. The pocket has an opening adjacent to the top surface.

17 Claims, 3 Drawing Sheets

(56) References Cited

U.S. PATENT DOCUMENTS

| | | | |
|---|---|---|---|
| 6,442,779 B1* | 9/2002 | LeVert | A47C 4/54 |
| | | | 5/648 |
| 6,490,742 B2* | 12/2002 | Hall | A61G 7/075 |
| | | | 128/845 |
| 6,634,045 B1* | 10/2003 | DuDonis | A47C 20/021 |
| | | | 5/632 |
| 6,640,368 B2* | 11/2003 | Roston | A47C 20/021 |
| | | | 5/648 |
| 6,935,697 B2* | 8/2005 | Conlon | A47C 16/02 |
| | | | 297/423.41 |
| 7,146,663 B2* | 12/2006 | Brown | A47D 13/08 |
| | | | 5/636 |
| 7,244,239 B2* | 7/2007 | Howard | A61F 5/3753 |
| | | | 128/878 |
| 8,286,285 B2* | 10/2012 | Mahler | A61F 5/01 |
| | | | 128/878 |
| 9,301,868 B2* | 4/2016 | Castle | A61G 7/0755 |
| 9,648,959 B2* | 5/2017 | Frydman | A47C 20/021 |
| 9,877,597 B2* | 1/2018 | Sclare | A47D 13/083 |
| 2002/0133881 A1* | 9/2002 | Vrbas | A47D 13/08 |
| | | | 5/655 |

* cited by examiner

PORTABLE MEDICAL ARMREST

TECHNICAL FIELD

This disclosure relates to a medical armrest, and more particularly to a portable medical armrest that can be used in a variety of locations.

BACKGROUND

Paramedics, nurses, doctors, and other caregivers often perform medical procedures on the arms of patients, such as administering intravenous medications, bandaging, inserting sutures or stitches, drawing blood, collecting blood samples, shaving cleaning or taking the patient's pulse. Health care professionals, such as paramedics and visiting nurses, also treat multiple patients per day in a variety of locations, including patients' homes, nursing facilities, and hospitals.

SUMMARY

To perform medical procedures, a sterile, stable surface on which to comfortably support the patient's arm is desirable. Due to a variety of locations where they may occur, a sterile and stable surface may not be readily available to support the patient's arm. It may therefore be desirable for such a surface to be portable.

Disclosed herein are implementations of portable medical apparatuses for supporting a patient's arm. According to a first implementation, the portable medical apparatus includes a top surface, a bottom surface, a peripheral surface, and an outer layer. The top surface has a front edge, a back edge located opposite from the front edge, and a concave depression extending into the top surface. The top surface slopes downward from the back edge to the front edge. The bottom surface is located opposite from the top surface, and the peripheral surface connects the top surface to the bottom surface. The outer layer is connected to a portion of the peripheral surface and defines a pocket between the outer layer and the portion of the peripheral surface. The pocket has an opening adjacent to the top surface.

The top surface, the bottom surface, the peripheral surface, and the outer layer can be made of material impervious to liquid. A strap can be connected to the bottom surface to removably connect the portable medical apparatus to an external object. The strap can be a hook and loop fastener comprising a first elongated strip connected to a first side of the bottom surface and a second elongated strip connected to a second side of the bottom surface opposing the first side. The bottom surface can include a bottom front edge, a bottom back edge located opposite the bottom front edge, a bottom first side edge, and a bottom second side edge. The bottom first side edge can be formed by the peripheral surface and be located adjacent to the bottom front edge and the bottom back edge. The bottom second side edge can be formed by the peripheral surface and be located opposite the bottom first side and adjacent to the bottom front edge and the bottom back edge. The bottom surface can define a recess extending into the bottom surface from the bottom first side edge to the bottom second side edge. The strap can be connected to the bottom surface inside of the recess.

The peripheral surface can include two pockets located on opposite edges of the peripheral surface. The peripheral surface can comprise four side surfaces that are substantially perpendicular to one another. The concave depression of the top surface can be one-half inch deep. The bottom surface can include a bottom front edge and a bottom back edge located opposite the bottom front edge. The bottom surface can define a bottom concave depression extending into the bottom surface from the bottom back edge to the bottom front edge. The bottom back edge can extend further way from the top surface than the bottom front edge. The bottom surface can be a substantially planar surface with the bottom front edge a substantially straight edge and the bottom back edge formed by a back leg extending away from the bottom surface in a direction opposite the top surface. The back leg can define a leg concave depression extending into the back leg between opposing side edges of the bottom surface, which are substantially perpendicular to the bottom front edge and the bottom back edge. The slope of the top surface can less than thirty percent. The concave depression defined by the top surface can extend an entire length from the back edge to the front edge.

According to a second implementation, a substantially rectangular prism for supporting a patient's arm comprises a top surface, a bottom surface, a hook and loop fastener, and a peripheral surface. The top surface has a front edge, a back edge substantially parallel to the front edge, and two side edges opposite one another and substantially perpendicular to the front edge and the back edge. The top surface defines a concave depression extending into the top surface from the back edge to the front edge. The bottom surface has a bottom front edge that is substantially straight, two bottom side edges opposite one another and substantially perpendicular to the bottom front edge, and a back leg opposite the bottom front edge. The back leg defines a leg concave depression extending into the back leg between the two bottom side edges. The back leg extends further away from the back edge of the top surface than the bottom front edge extends away from the front edge of the top surface. The bottom surface defines a recess extending into the bottom surface between the two bottom sides. The recess is substantially parallel to the bottom front edge.

The hook and loop fastener has a first elongated strip connected to a first side of the bottom surface and a second elongated strip connected to a second side of the bottom surface opposing the first side. The peripheral surface connects the top surface to the bottom surface. The peripheral surface has a front surface, a back surface opposite the front surface, and two side surfaces opposite one another. The front surface defines the front edge of the top surface and the bottom front edge of the bottom surface. The back surface defines the back edge of the top surface and the back leg of the bottom surface. The two side surfaces define the two side edges of the top surface and the top bottom side edges of the bottom surface. The side surfaces include pockets with openings adjacent to the top surface.

The top surface can be substantially perpendicular to the front surface, the back surface, and the two side surfaces of the peripheral surface. The front edge of the top surface can be closer to the bottom surface than the back edge of the top surface.

According to a third implementation, a portable medical apparatus for supporting a patient's arm includes a top surface, a bottom surface, a peripheral surface, and a pocket. The top surface has a front edge and a back edge opposite the front edge. The top surface defines a concave depression into the top surface that extends from the back edge to the front edge. The bottom surface is opposite the top surface and has a bottom front edge and a bottom back edge opposite the bottom front edge. The bottom surface defines a bottom concave depression extending into the bottom surface from the bottom back edge to the bottom front edge. The peripheral surface connects the top surface to the bottom surface. The pocket is attached to a portion of the peripheral surface and comprises an outer layer attached to the portion of the peripheral surface. The outer layer defines an opening between the outer layer and the portion of the peripheral surface that is adjacent to the top surface.

The front edge of the top surface can be closer to the bottom front edge of the bottom surface than the back edge of the top surface is to the bottom back edge of the bottom surface such that the top surface slopes downward from the back edge of the top surface to the front edge of the top surface when the bottom surface is substantially horizontal. The peripheral surface can be substantially perpendicular to the top surface. The bottom back edge of the bottom surface can be formed by a back leg that is substantially parallel to the bottom front edge and extends from the bottom surface in a direction opposite the top surface.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
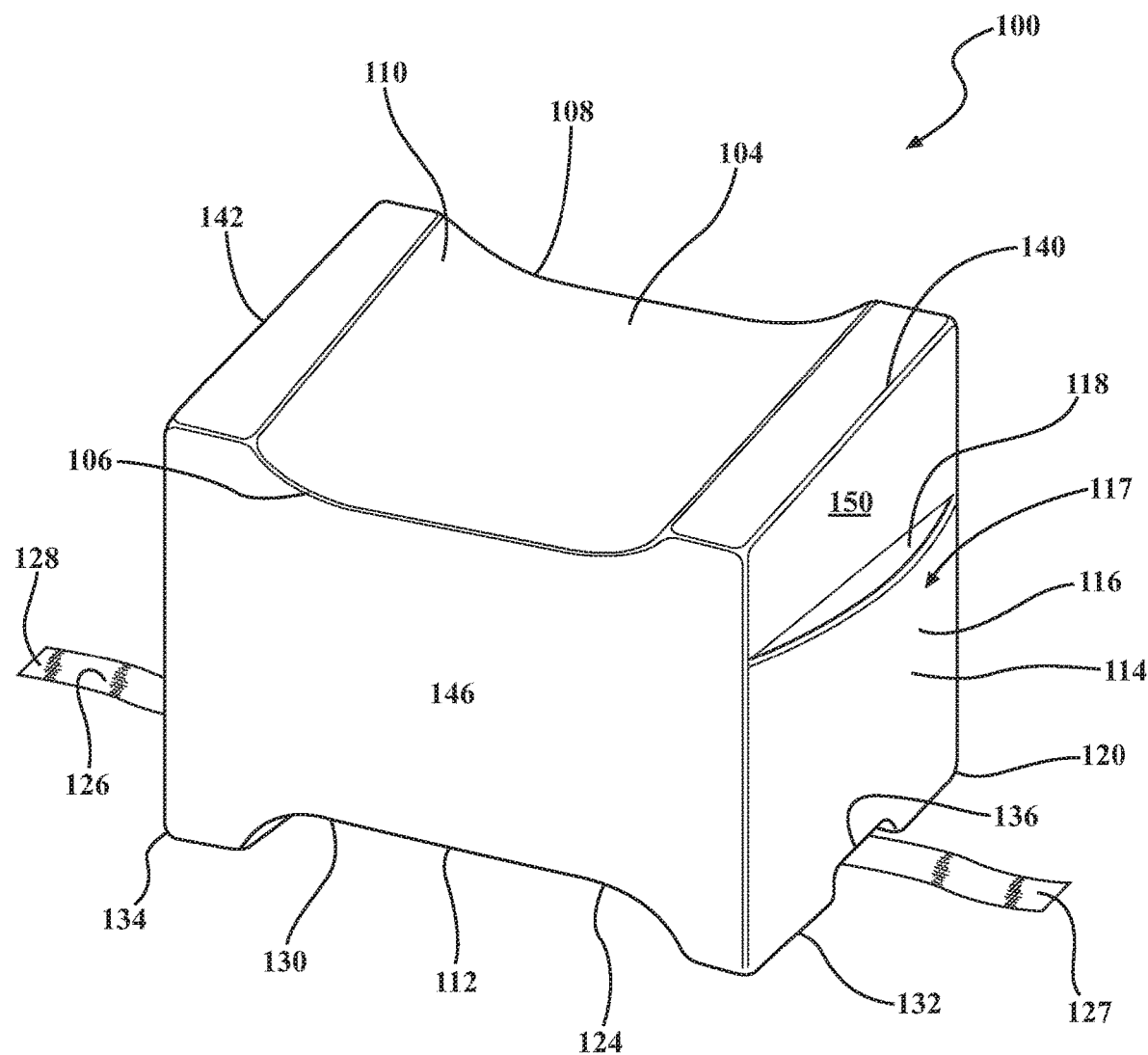
FIG. 1 is a perspective view of top, front, and right sides of a first implementation of a portable medical armrest.
Figure 2:
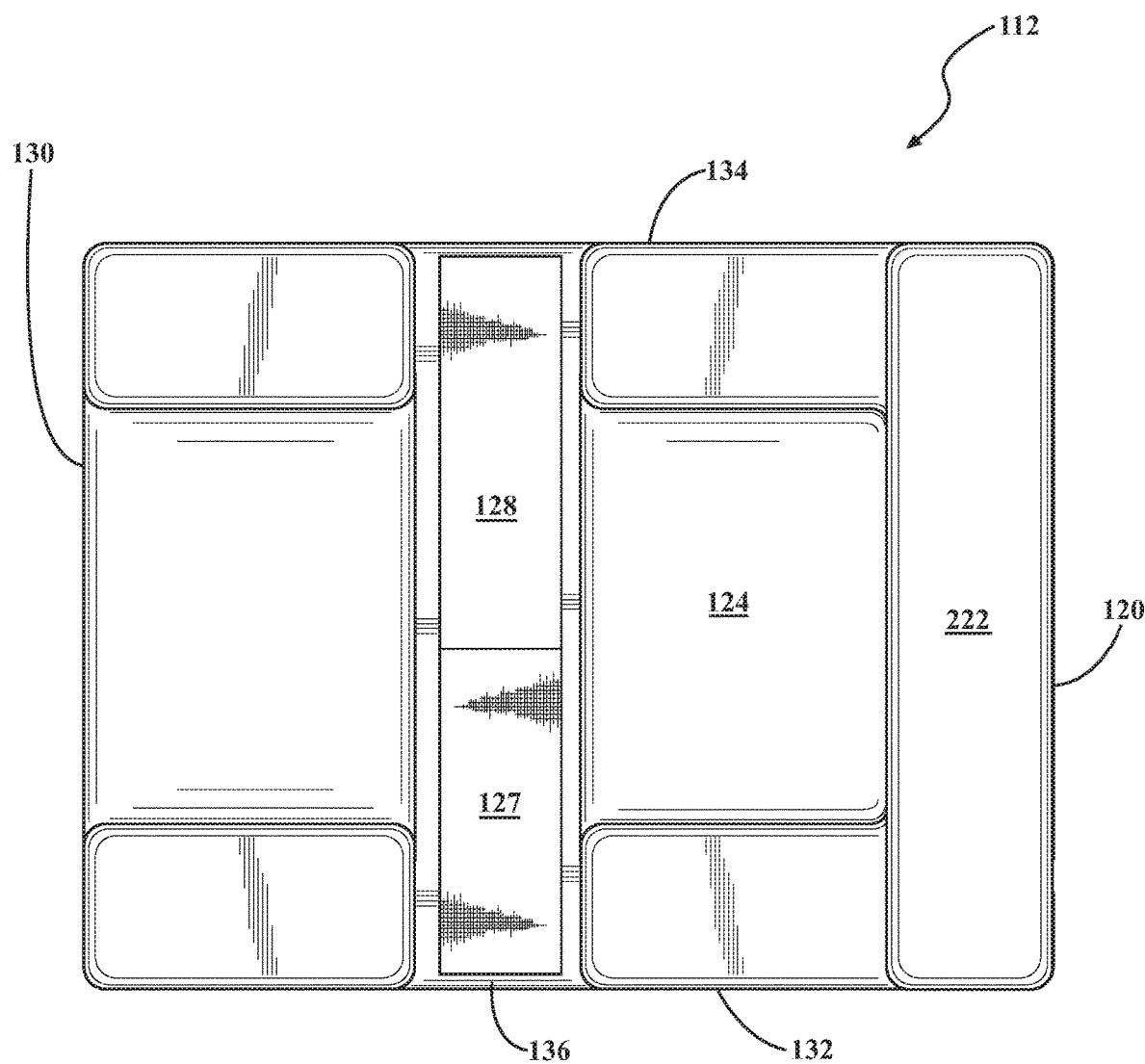
FIG. 2 is a bottom plan view of a second implementation of the portable medical armrest.
Figure 3:
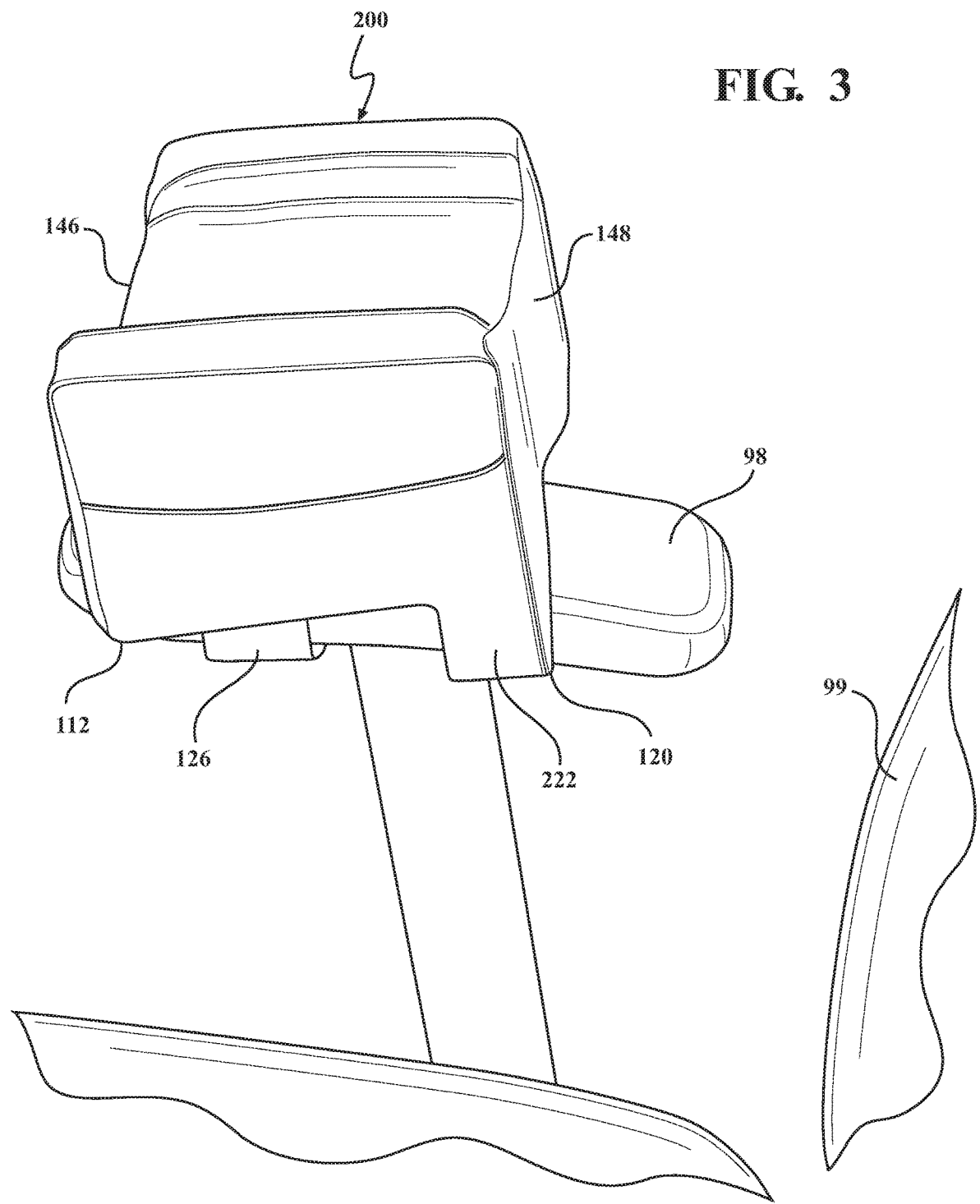
FIG. 3 is a perspective view of the second implementation of the portable medical armrest attached to an arm of a chair.

FIGS. 1-3 illustrate portable medical armrests that are adapted to be used in a variety of locations, including locations that otherwise lack a sterile and/or stable surface for a user, such as health care professional, to work. A portable medical armrest 100, such as the implementation shown in FIG. 1, can have a substantially rectangular prism configuration. Other configurations are possible. The portable medical armrest 100 can include a top surface 104 and a bottom surface 112 opposite the top surface 104. A peripheral surface 114 can connect the top surface 104 to the bottom surface 112. An outer layer 116 can be connected to a portion of the peripheral surface 114.

The top surface 104 can have a front edge 106, a back edge 108 located opposite from the front edge 106, and two side edges 140, 142 opposite one another. The front edge 106 and the back edge 108 can be substantially parallel to one another. The two side edges 140, 142 can be substantially perpendicular to the front edge 106 and the back edge 108. The top surface 104 can define a concave depression 110 extending into the top surface 104. The concave depression 110 can extend for an entire length of the top surface 104 from the front edge 106 to the back edge 108. The top surface 104 can also include a downward slope from the back edge 108 to the front edge 106. The downward slope of the top surface 104 can be approximately twenty percent (e.g., calculated as a percentage by dividing the rise by the run). In other embodiments, the downward slope of the top surface 104 can be between zero percent and thirty percent. The concave depression 110 can extend approximately one-half inch into the top surface 104. The concave depression 110 can also extend for a substantial width of the top surface 104 along the front edge 106 and the back edge 108. In other implementations, the concave depression 110 can extend more than one-half inch or less than one-half inch into the top surface 104. The concave depression 110 can also extend for any width of the top surface 104 along the front edge 106 and the back edge 108.

In the implementation shown in FIG. 1, the downward slope of the top surface 104 is achieved when the portable medical armrest 100 is on a substantially horizontal surface by having a bottom back edge 120 extending farther way from the top surface 104 than a bottom front edge 130. In other words, the distance between the bottom back edge 120 of the bottom surface 112 and the back edge 108 of the top surface 104 is greater than the distance between the bottom front edge 130 of the bottom surface 112 and the front edge 106 of the top surface 104.

The bottom back edge 120 of the bottom surface 112 is located opposite the bottom front edge 130. The bottom front edge 130 can be substantially straight, as opposed to the curved shape shown in FIG. 1. The bottom surface 112 can include a bottom first side edge 132, formed by the peripheral surface 114, located adjacent to the bottom front edge 130 and the bottom back edge 120. The bottom surface 112 can also include a bottom second side edge 134, formed by the peripheral surface 114, located opposite the bottom first side edge 132 and located adjacent to the bottom front edge 130 and to the bottom back edge 120. The bottom first side edge 132 and the bottom second side edge 134 can be substantially parallel to one another and substantially perpendicular to the bottom front edge 130 and the bottom back edge 120.

In some implementations, the bottom surface 112 can be a substantially planar surface. In the implementation illustrated in FIG. 1, the bottom surface 112 can define a bottom concave depression 124 extending into the bottom surface 112 for an entire length of the bottom surface 112 from the bottom back edge 120 to the bottom front edge 130. The bottom concave depression 124 allows the bottom surface 112 of the portable medical armrest 100 to be placed on a curved surface (e.g., the patient's leg) so that the top of that curved surface rests within the bottom concave depression 124. Oriented this way, the portable medical armrest 100 can stabilize the patient's arm placed on the top surface 104 so that the user can perform procedures on the patient's arm.

To allow a strap 126 to rest flush against the bottom surface 112 when the portable medical armrest 100 is placed on an external surface, the bottom surface 112 can also define a recess 136 extending into the bottom surface 112 from the bottom first side edge 132 to the bottom second side edge 134. The recess 136 can be substantially parallel to the bottom front edge 130 and the bottom back edge 120. The recess 136 can provide a space for the strap 126 to be connected to the bottom surface 112. In the illustrated, non-limiting implementation, the recess 136 has a substantially rectangular cross-sectional configuration. In other implementations, the recess 136 could be any length, width, or shape. In some implementations, the bottom surface 112 does not have a recess, so the strap 126 is not located in a recess.

The strap 126 can removably connect the portable medical armrest 100 to an external object, such as an arm 98 of a chair 99 (shown in FIG. 3). The strap 126 can comprise a first elongated strap 127 and a second elongated strap 128. The first elongated strap 127 can be connected to the bottom surface 112 near the bottom first side edge 132, and the second elongated strap 128 can be connected to the bottom surface 112 near the bottom second side edge 134. The first elongated strap 127 and the second elongated strap 128 can use any traditional means of fastening to be securely connected to the bottom surface 112 and removably connected to one another. For example, the first elongated strap 127 and the second elongated strap 128 could be sewn to the bottom surface 112 and then removably connected to one another using a hook and loop fastener. In other implementations, the strap 126 could include an elastic loop, an adhesive, a cam strap, a spring buckle strap, a ratchet strap, a side release buckle strap, a strap adjuster strap, a double ring strap, a flat hook strap, a wire hook strap, or any other type of fastening strap. The strap 126 may also be a single elongated strap attached to the bottom surface 112, with a removable second strap attaching to opposing sides of the single elongated strap. For example, the single elongated strap may be a hook and loop fastener sown to the bottom surface, and a similarly-sized elongated strap formed of a hook and loop fastener can be attached thereto for storage and for securing the portable medical armrest 100 to an external object.

The peripheral surface 114 can connect the top surface 104 to the bottom surface 112. If the peripheral surface 114 includes four perpendicular side surfaces, the portable medical armrest 100 can take the shape of a substantially rectangular prism. In other embodiments, the peripheral surface 114 can include any number of side surfaces forming any angle with the adjacent side surfaces, the top surface 104, and the bottom surface 112. For example, the peripheral surface 114 could include one round or ovaloid side surface, and the portable medical armrest 100 could take the shape of a disc or cylinder. The peripheral surface 114 could also include two, three, five, or more side surfaces and could cause the portable medical an rest 100 to take any prismatic shape. As shown, the peripheral surface 114 includes a front surface 146, a back surface 148 (shown in FIG. 3) opposite the front surface 146, and two side surfaces 150 substantially parallel to one another. The two side surfaces 150 are substantially perpendicular to the front surface 146 and the back surface 148.

The peripheral surface 114 can form any angle with the top surface 104 and the bottom surface 112. The peripheral surface 114 could be perpendicular to the top surface 104 or the bottom surface 112, as shown in the illustrated implementation. The peripheral surface 114 could also be non-perpendicular with the top surface 104 and bottom surface 112. For example, if the front edge 106 of the top surface 104 is closer to the bottom front edge 130 than the back edge 108 of the top surface 104 is to the bottom back edge 120 such that the top surface 104 forms a downward slope from the back edge 108 down to the front edge 106, the peripheral surface 114 could be non-perpendicular to the top surface 104.

The outer layer 116 can be connected to a portion of the peripheral surface 114. As shown, the outer layer 116 can be formed by a strip of fabric connected to a portion of the peripheral surface 114. The outer layer 116 can be connected to one of the side surfaces of the peripheral surface 114, such as one of the two side surfaces 150. The outer layer 116 can be connected to a substantial portion of the peripheral surface 114. The outer layer 116 can define a pocket 117 between the outer layer 116 and the portion of the peripheral surface 114, where the pocket 117 can have an opening 118 adjacent to the top surface 104. If the outer layer 116 includes a strip of fabric having four edges as shown, the strip of fabric can be connected to the portion of the peripheral surface 114 along three edges of the strip of fabric, leaving the fourth edge adjacent to the top surface 104 unconnected to the peripheral surface 114. The pocket 117 with the opening 118 along the unconnected edge of the strip of fabric adjacent to the top surface 104 can then be defined between the outer layer 116 and the portion of the peripheral surface 114. As shown in FIGS. 1 and 3, the pocket 117 may be flush with the top surface 104, or open below the top surface 104.

In other implementations, the peripheral surface 114 can omit the pockets 117 or have more than one pocket 117. For example, the peripheral surface 114 can include two pockets 117 located on opposite edges of the peripheral surface 114. This allows the portable medical armrest 100 to be used easily with both left- and right-handed medical providers. The size of the pocket 117 defined by the outer layer 116 and the portion of the peripheral surface 114 can be any size sufficient to support at least one test tube. Desirably, it is sized to support more than one test tube. The pocket 117 can be connected to any portion of the peripheral surface 114. In alternative embodiments, a container (not shown) defining its own internal space could be attached to a portion of the peripheral surface 114 instead of the outer layer 116.

Surfaces of the portable medical armrest 100, including the top surface 104, the bottom surface 112, the peripheral surface 114, and the outer layer 116, can be made of material impervious to liquid such as artificial leather, or any natural or synthetic fabric that is laminated or coated with a waterproofing material such as rubber, polyvinyl chloride, polyurethane, silicone elastomer, fluoropolymers, or wax. The user of the portable medical armrest 100 may regularly encounter blood, dirt, sweat, oil, and other contaminants while interacting with patients. When each surface of the portable medical armrest 100 is made of material imperious to liquid, the portable medical armrest 100 can be easily cleaned so that the portable medical armrest 100 is sterile before being used on another patient. Making the portable medical armrest 100 of material impervious to liquid also ensures liquid contaminants, such as blood, are not absorbed into the portable medical armrest 100 where the liquid contaminant could come into contact with another patient during a subsequent use.

In other implementations, the surfaces of the portable medical armrest 100, including the top surface 104, the bottom surface 112, the peripheral surface 114, and the outer layer 116, can be made of material that is not impervious to liquid including any natural or synthetic fabric. The top surface 104, the bottom surface 112, the peripheral surface 114, and the outer layer 116 can also be made of different materials. For example, the top surface 104, the bottom surface 112, and the peripheral surface 114 can be made of artificial leather, while the outer layer 116 can be made of plastic. The interior of the portable medical armrest 100 can be filled with foam, such as polyurethane, polyethylene, lux, latex rubber, or open cell or closed cell foam. Filling the portable medical armrest 100 with foam allows the top surface 104 to support a patient's arm when the bottom surface 112 is placed on an exterior surface. In alternative implementations, the interior of the portable medical armrest 100 could be filled with material other than foam, such as rubber or plastic. Desirably, the material is light-weight. The interior of the portable medical armrest 100 may also not be filled with any material if the peripheral surface 114 sufficiently supports the top surface 104 and the patient's arm.

The peripheral surface 114 can be connected to the top surface 104 and the bottom surface 112 using sewing stitching adhesive, bonding welding mechanical fastening or any other known means of connecting surfaces together. The outer layer 116 can be connected to the portion of peripheral surface 114 using any of the listed processes. The surfaces of the portable medical armrest 100 can also be connected using one or more connecting processes.

A portable medical armrest 200 according to a second implementation is shown in FIGS. 2 and 3. The portable medical armrest 200 is substantially similar as the portable medical armrest 100 except for a back leg 222 extending away from the bottom back edge 120 of the bottom surface 112 in a direction opposite the top surface 104. The back leg 222 serves to prop up the top surface 104 of the portable medical armrest 200 so that the downward slope between the front edge 106 and the back edge 108 is created when the portable medical armrest 200 is placed on an external surface.

The back leg 222 can be substantially parallel to the bottom front edge 130. The bottom concave depression 124 defined by the bottom surface 112 can extend through the back leg 222 so that the top of one of the patient's leg fits into the bottom concave depression 124. The back leg 222 can have a substantially rectangular prism configuration as shown. Alternatively, the back leg 222 could be formed of any shape, such as any type of prism, cylinder, cone, or sphere, and could have any base shape such as triangular, rectangular, or ovaloid, In other implementations, the back leg 222 could include multiple back legs 222 extending away from the bottom surface 112 in the direction opposite from the top surface 104 and could be connected to portions of the bottom back edge 120 of the bottom surface 112.

To use any implementation of the portable medical armrest 100, 200, the portable medical armrest 100, 200 is placed on an external surface, such as the arm of a chair, a table, a counter top, a patient's leg, or a desk. The portable medical armrest 100, 200 is oriented so that the bottom surface 112 is placed on the external surface with the back edge 108 of the top surface 104 facing the patient's torso. This results in the downward slope in the top surface 104 extending away from the patient, which allows the patient to hold his or her arm on the portable medical armrest 100, 200 in a more natural position.

If the external surface is substantially horizontal and can sufficiently support to adequately secure the portable medical armrest 100, 200, the strap 126 can be placed within the recess 136 so that the portable medical armrest 100, 200 rests substantially flush on the external surface. Example of such external supports are counter tops and table tops. If the external surface is substantially horizontal but does not provide sufficient support to adequately secure the portable medical armrest 100, 200, the strap 126 can be used to secure the portable medical armrest 100, 200 to the external surface. An example of such an external support is the arm 98 of the chair 99, as shown in FIG. 3. The strap 126 is used by disconnecting the first elongated strap 127 from the second elongated strap 128 and placing a portion of the external support, such as the arm 98 of the chair 99, between the strap 126 and the bottom surface 112 of the portable medical armrest 100, 200. The first elongated strap 127 and the second elongated strap 128 can then be reconnected.

When one of the patient's legs is used as the external support, the bottom surface 112 of the portable medical armrest 100, 200 can be rested on the patient's leg so that the leg extends longitudinally through the bottom concave depression 124. The strap 126 can be connected to the patient's leg. Alternatively, the strap 126 can be placed within the recess 136 so that the portable medical armrest 100, 200 rests substantially flush against the patient's leg.

Once the portable medical armrest 100, 200 is secured on the external surface, the patient can place his or her arm onto the top surface 104 of the portable medical armrest 100, 200. The concave depression 110 guides the patient's arm onto the top surface 104 and ensures that the patient's arm remains physically comfortable. The concave depression 110 also supports and stabilizes the patient's arm on the top surface 104 and restricts the arm's movement in relation to the portable medical armrest 100, 200. The restriction of the arm's movement can allow a health care professional, such as a paramedic, nurse, doctor, or other caregiver, to more easily perform procedures on the patient's arm. Such procedures can include administering intravenous medicines, bandaging, inserting sutures or stitches, drawing blood, collecting blood samples, shaving, cleaning taking the patient's pulse, or any other procedure that can be performed on the arm. The pocket 117 defined by the outer layer 116 and the peripheral surface 114 can be used by the user of the portable medical armrest 100, 200 to easily store, transport, and access equipment necessary for performing procedures on the patient, such as blood collection tubes, needles, needle holders, syringes, gloves, medications, medical gauze, bandages, intravenous kits, suture kits, or tubing.

While the invention has been described in connection with certain embodiments, it is to be understood that the invention is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A portable medical apparatus for supporting a patient's arm, the portable medical apparatus comprising:
   a top surface having a front edge and a back edge opposite the front edge, wherein the top surface defines a concave depression extending into the top surface that extends an entire length from the back edge to the front edge, and the concave depression slopes downward for the entire length from the back edge to the front edge;
   a bottom surface opposite the top surface;
   a peripheral surface connecting the top surface to the bottom surface; and
   an outer layer connected to a portion of the peripheral surface, the outer layer defining a pocket between the outer layer and the portion of the peripheral surface, the pocket having an opening adjacent to the top surface, wherein the bottom surface comprises:
   a bottom front edge; and
   a bottom back edge located opposite the bottom front edge, the bottom back edge extending further away from the top surface than the bottom front edge.

2. The portable medical apparatus of claim 1, wherein the top surface, the bottom surface, the peripheral surface, and the outer layer are made of material impervious to liquid.

3. The portable medical apparatus of claim 1, comprising a strap connected to the bottom surface, wherein the strap removably connects the portable medical apparatus to an external object.

4. The portable medical apparatus of claim 3, wherein the strap is a hook and loop fastener comprising a first elongated strip connected to a first side of the bottom surface and a second elongated strip connected to a second side of the bottom surface that opposes the first side.

5. The portable medical apparatus of claim 3, wherein the bottom surface comprises:
   a bottom first side edge, formed by the peripheral surface, located adjacent to the bottom front edge and the bottom back edge; and a bottom second side edge, formed by the peripheral surface, located opposite the bottom first side edge and located adjacent to the bottom front edge and the bottom back edge, wherein the bottom surface defines a recess extending into the bottom surface from the bottom first side edge to the bottom second side edge and the strap is connected to the bottom surface inside of the recess.

6. The portable medical apparatus of claim 1, wherein the peripheral surface comprises two pockets located on opposite edges of the peripheral surface.

7. The portable medical apparatus of claim 1, wherein the peripheral surface comprises four side surfaces that are substantially perpendicular to one another.

8. The portable medical apparatus of claim 1, wherein the concave depression of the top surface is one half-inch deep.

9. The portable medical apparatus of claim 1, wherein the bottom surface defines a bottom concave depression extending into the bottom surface from the bottom back edge to the bottom front edge.

10. The portable medical apparatus of claim 1, wherein the bottom front edge is a substantially straight edge, and the bottom back edge is formed by a back leg extending away from the bottom surface in a direction opposite the top surface.

11. The portable medical apparatus of claim 10, wherein the back leg defines a leg concave depression extending into the back leg between opposing side edges of the bottom surface, the opposing side edges being substantially perpendicular to the bottom front edge and the bottom back edge.

12. The portable medical apparatus of claim 1, wherein the top surface slopes downward less than thirty percent.

13. A substantially rectangular prism for supporting a patient's arm comprising:
    a top surface having a front edge, a back edge substantially parallel to the front edge, and two side edges oppose one another and substantially perpendicular to the front edge and the back edge, wherein the top surface defines a concave depression extending into the top surface from the back edge to the front edge;
    a bottom surface having a bottom front edge that is substantially straight, two bottom side edges opposite one another and substantially perpendicular to the bottom front edge, and a back leg opposite the bottom front edge, wherein the back leg defines a leg concave depression extending into the back leg between the two bottom side edges, wherein the back leg extends further away from the back edge of the top surface than the bottom front edge extends away from the front edge of the top surface, and wherein the bottom surface defines a recess extending into the bottom surface between the two bottom side edges, the recess being substantially parallel to the bottom front edge;
    a hook and loop fastener having a first elongated strip connected to a first side of the bottom surface and a second elongated strip connected to a second side of the bottom surface opposing the first side; and
    a peripheral surface connecting the top surface to the bottom surface, the peripheral surface comprising a front surface, a back surface opposite the front surface, and two side surfaces opposite one another, wherein the front surface defines the front edge of the top surface and the bottom front edge of the bottom surface, wherein the back surface defines the back edge of the top surface and the back leg of the bottom surface, wherein the two side surfaces define the two side edges of the top surface and the two bottom side edges of the bottom surface, and wherein the side surfaces comprise pockets with openings adjacent to the top surface.

14. The substantially rectangular prism of claim 13, wherein the top surface is substantially perpendicular to the front surface, the back surface, and the two side surfaces of the peripheral surface.

15. The substantially rectangular prism of claim 13, wherein the front edge of the top surface is closer to the bottom surface than the back edge of the top surface.

16. A portable medical apparatus for supporting a patient's arm, the portable medical apparatus comprising:
    a top surface having a front edge and a back edge opposite the front edge, wherein the top surface defines a concave depression into the top surface that extends from the back edge to the front edge;
    a bottom surface opposite the top surface, the bottom surface having a bottom front edge and a bottom back edge opposite the bottom front edge, wherein the bottom surface defines a bottom concave depression extending into the bottom surface from the bottom back edge to the bottom front edge;
    a peripheral surface connecting the top surface to the bottom surface;
    at least one layer of material enclosing the top surface, the bottom surface, and the peripheral surface; and
    an outer layer secured about a portion of its peripheral edge to the material adjacent to the peripheral surface and defining a pocket with single opening between the outer layer and the material that lies substantially parallel to the top surface, wherein the front edge of the top surface is closer to the bottom front edge of the bottom surface than the back edge of the top surface is to the bottom back edge of the bottom surface such that the top surface slopes downward from the back edge of the top surface to the front edge of the top surface when the bottom surface is substantially horizontal.

17. The portable medical apparatus of claim 16, wherein the peripheral surface is substantially perpendicular to the top surface, the bottom back edge of the bottom surface is formed by a back leg substantially parallel to the bottom front edge, and the back leg extends from the bottom surface in a direction opposite the top surface.

* * * * *